(12) United States Patent
Skerl et al.

(10) Patent No.: US 8,652,048 B2
(45) Date of Patent: Feb. 18, 2014

(54) IMPLANT AND SYSTEM FOR PREDICTING DECOMPENSATION

(75) Inventors: Olaf Skerl, Bad Doberan (DE); Michael Lippert, Ansbach (DE)

(73) Assignee: Biotronik SE & Co. KG (DE)

( * ) Notice: Subject to any disclaimer, the term of this patent is extended or adjusted under 35 U.S.C. 154(b) by 231 days.

(21) Appl. No.: 13/186,511

(22) Filed: Jul. 20, 2011

(65) Prior Publication Data

US 2012/0035453 A1 Feb. 9, 2012

Related U.S. Application Data

(60) Provisional application No. 61/371,177, filed on Aug. 6, 2010.

(51) Int. Cl.
*A61B 8/00* (2006.01)

(52) U.S. Cl.
USPC .......... 600/438; 600/437; 600/407; 600/481; 600/483

(58) Field of Classification Search
None
See application file for complete search history.

(56) References Cited

U.S. PATENT DOCUMENTS

| | | | |
|---|---|---|---|
| 6,405,085 B1 | 6/2002 | Graupner et al. | |
| 7,395,114 B2 | 7/2008 | Czygan et al. | |
| 7,479,112 B2 * | 1/2009 | Sweeney et al. | 600/528 |
| 7,519,422 B2 | 4/2009 | Lippert et al. | |
| 7,570,990 B2 | 8/2009 | Faber et al. | |
| 7,593,766 B2 | 9/2009 | Faber et al. | |
| 7,702,389 B2 | 4/2010 | Czygan et al. | |
| 7,844,335 B2 | 11/2010 | Lippert et al. | |
| 7,883,469 B2 | 2/2011 | Lippert et al. | |
| 2002/0123674 A1 | 9/2002 | Plicchi et al. | |
| 2002/0156379 A1* | 10/2002 | Angelsen et al. | 600/459 |
| 2008/0157980 A1 | 7/2008 | Sachanandani et al. | |

* cited by examiner

*Primary Examiner* — Long V. Le
*Assistant Examiner* — Farshad Negarestan
(74) *Attorney, Agent, or Firm* — Craig A. Fieschko, Esq.; DeWitt Ross & Stevens S.C.

(57) ABSTRACT

An implant predicts decompensation of a patient's heart based on an acoustic pressure measurement. The implant includes first and second acoustic transducers, which are matched to each other and which rest in/on the patient's thorax. The first acoustic transducer emits an acoustic signal which has at least one first signal portion having a first frequency. The second acoustic transducer is designed to receive and re-emit the emitted acoustic signal, or to reflect it, such that the first acoustic transducer receives the emitted acoustic signal. A signal processing unit communicates with at least one of the two acoustic transducers and determines an attenuation value as a function of the attenuation of the received acoustic signal versus the originally emitted acoustic signal, and provides a prediction signal as a function of a comparison of the attenuation value to a threshold value, wherein the prediction signal indicates the development of decompensation.

19 Claims, 1 Drawing Sheet

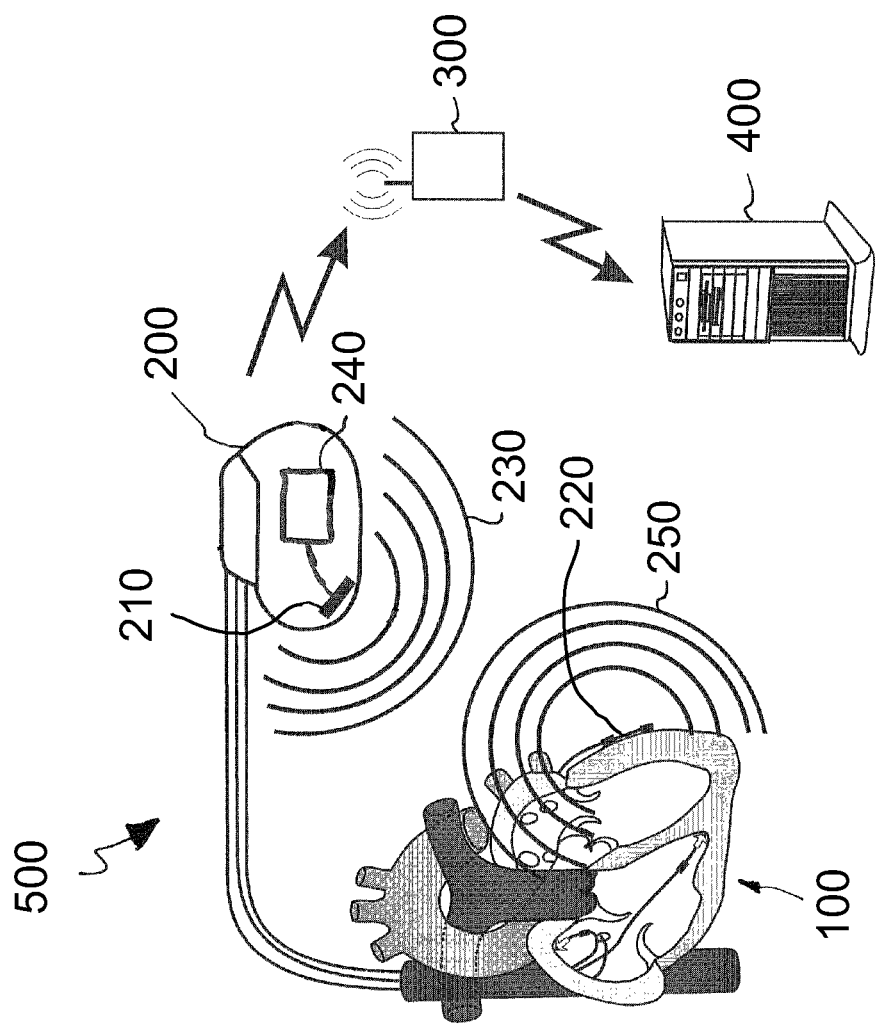

IMPLANT AND SYSTEM FOR PREDICTING DECOMPENSATION

CROSS-REFERENCE TO RELATED APPLICATIONS

This application claims priority under 35 U.S.C. §119(e) to U.S. Provisional Patent Application 61/371,177 filed Aug. 6, 2010, the entirety of which is incorporated by reference herein.

FIELD OF THE INVENTION

The invention generally relates to the field of implantable medical devices for predicting cardiovascular abnormalities. More specifically, the invention relates to a system for predicting decompensation, including an implant for predicting decompensation of a patient's heart based on a measurement of acoustic tissue properties.

BACKGROUND OF THE INVENTION

Devices for predicting cardiovascular abnormalities are known, and are often integrated into (or connected to) an implanted cardiac pacemaker or cardioverter/defibrillator. It is desirable to design these prediction devices such that they predict a dysfunction of the cardiovascular system well in advance of the dysfunction, and with high specificity.

Implants for predicting decompensation of the heart of a patient are known, such as from US Patent Appl'n. Publ'n. 2008/0157980. Some of these implants perform prediction based on the detection of a parameter having a value dependent on a rate of fluid in the lungs of the patient. It is known that the buildup of water in pulmonary tissue is an indicator of imminent decompensation. A known approach is to quantify the rate of fluid in the pulmonary tissue by capturing transthoracic electrical impedance. The disadvantage here is that the electrical conductivity of the blood, which is subject to natural fluctuations, has considerable influence on the impedance measurement, so that prediction devices based on this approach have a comparatively low specificity.

Another way to determine the rate of fluid in pulmonary tissue is to determine the sound velocity of an acoustic signal passing through the lungs of the patient. It is known that the sound velocity is dependent on the density of the medium through which the sound wave travels. Unfortunately, this method suffers from the disadvantage that the sound velocity is dependent not only on the rate of fluid in the pulmonary tissue, but also highly dependent on the breathing cycle, i.e., the fluctuation of the air volume in the lungs. This principle has further disadvantages, which will be described below.

A prediction device which operates via the acoustic method is described in Patent Appl'n. Publ'n. US 2002/0123674 A1. The sound velocity is determined by way of travel time measurement, and the reference describes the travel time of an ultrasonic pulse being in the range of 10 to 100 μs. In order to be able to detect fluid buildup in the pulmonary tissue and an associated change in the travel time, the signal processor in the described prediction device must have a resolution of approximately 100 ns, which is difficult to achieve without significant complexity. Additionally, a change in the travel time of this magnitude could be caused by a change in the distance between the transmitter and receiver of approximately 0.1 mm. As a result, the exact distance between the transmitter and receiver must be known in order to be able to provide reliable information about the change in sound velocity. Very small changes in the distances, such as those caused by a natural change in the size of the lungs or by variably deep breathing processes, can result in travel time changes, which can be mistaken for a change in the sound velocity and thereby possibly fluid buildup in the pulmonary tissue. Thus, a prediction device of this type tends to exhibit low specificity, particularly after an extended idle time during which component distance changes tend to occur. This disadvantage, as well as the need for a complex signal processing system, decreases the suitability of the acoustic method for implementation in implantable medical devices.

SUMMARY OF PREFERRED VERSIONS OF THE INVENTION

The invention seeks to provide an implant for predicting decompensation of the heart of a patient, which requires limited circuit-related complexity and at the same time exhibits high specificity. A preferred version of the implant includes two acoustic transducers and a signal processing unit. The first acoustic transducer and the second acoustic transducer are matched to each other, and both are designed to be situated in or on the thorax of the patient. The first acoustic transducer is designed to emit an acoustic signal which has at least one first signal portion having a first frequency. The second acoustic transducer is designed to receive the emitted acoustic signal or to reflect it such that the first acoustic transducer can receive the emitted acoustic signal. The signal processing unit is operatively connected to at least one of the two acoustic transducers, and is designed to determine an attenuation value as a function of an attenuation of a received acoustic signal compared to an originally emitted acoustic signal. The signal processing unit then provides a prediction signal, generated as a function of a comparison of the attenuation value to a threshold value, which is suited to indicate the development of decompensation.

The invention is based on the realization that attenuation of an acoustic signal in pulmonary tissue is a parameter having a value which is not only heavily dependent on the fluid content of the pulmonary tissue, but is also frequency-dependent. More specifically, attenuation increases as the frequency of the sound rises.

Preferably, the attenuation a of a signal is determined based on the formula provided below:

$$a = 10 \log \frac{J(r)}{J_0} = -\alpha \cdot f^k \cdot r, \quad (1)$$

where $J(r)$ is the sound intensity dependent on a propagation distance r and $J_0$ is the sound intensity of the signal for $r=0$. $\alpha$ is a material-dependent attenuation coefficient, f is the frequency of the signal, and k is a number between 1 and 2.

The attenuation value determined by the signal processing unit is dependent on the attenuation coefficient which is present between the two acoustic transducers. The attenuation coefficient $\alpha$ is a material property and varies considerably between different media, as the table below shows:

| Medium | $\alpha$ in dB/(cm · MHz) |
|---|---|
| Water | 0.002 |
| Blood | 0.03 |
| Soft tissue | 0.3 |
| Air | 12 |

The values for the attenuation coefficient α stated in the table above should be understood as representative mean values.

The inventors have recognized that a rise in the rate of fluid in the lungs of the patient, and consequently the development of decompensation, can be detected by way of an attenuation coefficient present in the thorax. The attenuation coefficient decreases as the fluid buildup in the lungs increases.

It is advantageous that the attenuation coefficient of water is several times lower than the attenuation coefficient of air. Thus, rising water content in the pulmonary tissue directly and considerably affects the attenuation coefficient. It is furthermore advantageous that the attenuation coefficient is substantially independent from the electrolyte balance of the patient as well as the packed cell volume. In this way, a received acoustic signal clearly differs from any interfering signals that may be present. The implant therefore achieves a prediction signal having particularly high specificity.

The attenuation coefficient serves as a measure of the fluid buildup in the lungs, and decreases when the fluid in the lungs increases, and rises when the fluid in the lungs decreases. If the attenuation value determined by the signal processing unit drops below the threshold value, the signal processing unit preferably emits a prediction signal which indicates the development of cardiac decompensation.

A particular advantage of the implant is that no knowledge of the exact distance of the two acoustic transducers and no exact alignment of the acoustic transducers are required in order to issue the prediction signal. A small change in the distance at best causes an insignificant change in the attenuation of the received acoustic signal and does not result in the output of a prediction signal that is indicative of decompensation onset. In addition, acoustic transducers having broad directional characteristics may be used, which keeps the manufacturing costs of the implant low and simplifies the implantation of the implant in the patient.

The second acoustic transducer can be an active acoustic transducer, which is designed to convert a received acoustic signal into another signal (for example into an electrical signal), or a passive acoustic transducer, such as a reflector which is designed to reflect an emitted acoustic signal back to the first acoustic transducer. The first acoustic transducer is an active acoustic transducer and can be implemented, for example, as a piezo crystal, piezoelectric polymer or micromechanical transducer. If the second acoustic transducer is likewise an active acoustic transducer, it can also be implemented, for example, as a piezo crystal, piezoelectric polymer or micromechanical transducer. If the second acoustic transducer is a passive reflector, it is designed in terms of shape, configuration and/or material such that it reflects an incoming acoustic signal emitted by the first acoustic transducer back to the first acoustic transducer. In a preferred version of the invention, the second acoustic transducer is formed by a casing comprising a plurality of gas bubbles.

The two acoustic transducers are preferably designed to be disposed in/on the patient such that at least part of the lungs of the patient is located between them.

Preferably, the first acoustic transducer is disposed in a housing of the implant, and the second of the two acoustic transducers is disposed outside of the housing of the implant. For example, the second acoustic transducer may be a reflector located outside of the housing of the implant, and can reflect an acoustic signal emitted by the first acoustic transducer back to the first acoustic transducer. In this version of the invention, the first acoustic transducer is also a transmitting and receiving acoustic transducer which is operatively connected to the signal processing unit.

In another version, the first and the second acoustic transducers are both located outside of the housing of the implant. Other arrangements are also possible. For example, rather than the first acoustic transducer being a transmitting acoustic transducer and the second acoustic transducer being a receiving acoustic transducer, an opposite arrangement is possible. Similarly, rather than the first acoustic transducer being a transmitting and receiving acoustic transducer and the second acoustic transducer being a reflector, the reverse arrangement might be used.

Arrangements using a reflector have the advantage that only the transmitting and receiving acoustic transducer has to be operatively connected to the signal processing unit, for example by a cable or wirelessly. The reflector does not have to be connected to the signal processing unit, which is advantageous for the placement of the reflector. For example, it can be placed on or integrated within an ICD (implantable cardioverter/defibrillator) electrode. In one optional arrangement, the reflector is integrated in or placed on a stent of the patient.

In one version, the transmitting power of the first acoustic transducer is constant. In another version, the implant is designed to adjust and set the transmitting power as a function of the determined attenuation value.

Throughout this document, an acoustic signal shall mean a sound signal. It need not be audible, and the first frequency of the first signal portion is preferably in the ultrasonic frequency range, most preferably in the frequency range of 30 kHz to 10 MHz.

In one version of the invention, the first acoustic transducer emits an acoustic signal having a high first frequency, preferably 100 kHz or more. This has the advantage that the attenuation of a received acoustic signal is comparatively strong.

Further versions of the implant will be described hereinafter. The additional characteristics of these further versions can be combined with each other and/or with characteristics described above so as to form other versions, unless they are expressly described as being alternatives of each other.

In a preferred version, the first acoustic transducer is designed to emit an acoustic signal which has a first signal portion having a first frequency, and a second signal portion having a second frequency which is different from the first frequency. In this version, the signal processing unit is designed to determine an attenuation value as a function of an attenuation of the first signal portion and an attenuation of the second signal portion in a received acoustic signal, as compared to the first signal portion or the second signal portion in an originally emitted acoustic signal.

By suitably comparing the changes of the two signal portions of the received acoustic signal with respect to the emitted acoustic signal, the implant issues a prediction signal that exhibits increased specificity compared to the implant conducting a single-frequency measurement, and additionally this signal is provided well in advance of significant decompensation, in the case of very low fluid buildup in the lungs.

With the multi-frequency method, the requirements for the signal processing unit to determine the attenuation value are low, which results in a small design of the implant. Contrary to known prediction devices, the implant requires no exact, predeterminable reference value for the attenuation coefficient or knowledge of the precise distance between the two acoustic transducers in order to determine the amounts of attenuation of the two signal portions. To determine the attenuation value, the signal processing unit can perform an amplitude measurement or sound intensity measurement for the two received signal portions.

A further advantage of this version is that it can compensate for changes in an emission signal strength of the acoustic signal and changes in a detection sensitivity of the first or second acoustic transducer, which could potentially result in the output of incorrect prediction signals. This is done by using an attenuation amount of the first or second signal portion as a reference value for the attenuation amount of the other signal portion. In this manner, this version lowers the influence of further disturbance variables, such as fluctuating emission signal strength, changing detection sensitivity, a changing angle between an orientation of the first or second acoustic transducer to the directional characteristics of the other acoustic transducer, change in the distance between the two acoustic transducers, aging effects, or fluctuations of a battery voltage present in the implant. This advantageous effect is supported when the directional characteristics of the first and second acoustic transducers are approximately equal for the first and second frequencies. In a preferred version, the directional characteristics of the first acoustic transducer are approximately identical for the first and second frequencies, and the directional characteristics of the second acoustic transducer are at least approximately identical for the first and second frequencies.

The signal processing unit in this version is preferably designed to determine the attenuation value as a function of a ratio of the attenuation of the first signal portion to the attenuation of the second signal portion. For example, the signal processing unit determines the attenuation value such that it measures a difference in the attenuation of the two signal portions.

The first frequency of the first signal portion and the second frequency of the second signal portion are preferably in the ultrasonic frequency range, most preferably in the frequency range of 30 kHz to 10 MHz.

In an exemplary version, the first acoustic transducer is designed to first emit a first signal portion having a first frequency and thereafter emit a second signal portion having a second frequency. This version simplifies signal processing in the signal processing units. The receiving acoustic transducer is preferably designed to receive an acoustic signal in a time period in which the arrival of the emitted acoustic signal is expected. In this way, the influence of disturbance variables is again reduced. To this end, the first acoustic transducer is designed to emit the second signal portion directly after emitting the first signal portion, whereby it can be assumed for the subsequent determination of the attenuation value that the distance between the two acoustic transducers is approximately equally large for both signal portions.

In one version, the first and the second frequencies considerably differ from each other, for example, the first frequency is considerably lower than the second frequency. The first frequency and the second frequency preferably differ from each other by a factor of approximately eight. This ratio is comparatively easy to implement in terms of circuitry. For example, the first frequency may be approximately 50 kHz and the second frequency may be approximately 400 kHz. At a frequency of approximately 50 kHz, acoustic attenuation in the lungs is comparatively low. As a result, the attenuation amount of the signal portion having this frequency is well suited as a reference value for the attenuation amount of the other signal portion having the higher frequency. At a frequency of approximately 400 kHz, the attenuation amount is highly dependent on the water content in the lungs.

In a further version, the first acoustic transducer is designed to emit the first signal portion having the first frequency and the second signal portion having the second frequency at approximately the same time.

In another version, the first acoustic transducer is designed to emit the acoustic signal in a form that is very similar to a Dirac pulse function, that is, in the form of a pulse having a very short pulse duration. The pulse duration, for example, can be just a few microseconds, such as 20 to 40 μs. An acoustic signal in the form of such a short pulse has a wide spectrum, which also comprises a first signal portion having the first frequency and a second signal portion having the second frequency.

The various versions of the implants preferably include a filter connected upstream of the signal processing unit, with the filter being designed to divide a received acoustic signal into a first signal portion having a first frequency and a second signal portion having a second frequency, so that the signal processing unit has the first signal portion and the second signal portion available for separate processing. The filter therefore has the advantage that it is ensured that the signal processing unit can process and evaluate the first signal portion and the second signal portion separate from each other. For example, the filter can include two band pass filters connected in parallel to each other and which are supplied an acoustic signal emitted by the first acoustic transducer. The first band pass filter only allows portions of the received acoustic signal having the first frequency to pass, and the second band pass filter allows only signal portions of the received acoustic signal having the second frequency to pass.

In another preferred version, the signal processing unit is designed to determine the attenuation value as a function of an extension of a pulse duration of a received acoustic signal compared to the pulse duration of an originally emitted acoustic signal. The inventors have recognized that the attenuation of an emitted acoustic signal causes not only a reduction in the amplitude of the acoustic signal, but also an extension of the pulse duration of the pulse. The extension of the pulse duration can be explained in terms of the frequency domain such that the attenuation of an emitted signal is dependent on the frequency, and high-frequency signal portions are attenuated more strongly than low-frequency signal portions. In the time domain, this is expressed in the form of pulse extension. The degree of the extension is dependent on the attenuation coefficient present between the two acoustic transducers. This version is particularly preferred when the first acoustic transducer emits the acoustic signal in the form of a short and broadband pulse.

The implant may include a position sensor designed to supply a position signal depending on the position of the patient. In this version, the signal processing unit is designed to output the prediction signal as a function of the position signal and the determined attenuation value. This version has the advantage that the prediction signal is output, for example, only for certain positions of the patient, such as lying or standing, so that the prediction signal exhibits further increased specificity.

In addition, signal processing in one version is controlled so as to carry out a determination of the attenuation value only for certain values of the position signal. In this way, attenuation values can be classified.

In this document, an "activity sensor," which determines a patient's activity such as resting or walking, can also be provided by a position sensor.

The signal processing unit is preferably designed to determine a first amplitude value as a function of a first amplitude of a first signal portion having a first frequency, and a second amplitude value as a function of a second amplitude of a second signal portion having a second frequency for a received signal, and to determine the attenuation value as a function of the determined first and the determined second amplitude values.

Because the attenuation coefficient present between the two acoustic transducers is approximately equally large for both signal portions, the signal processing unit is designed to determine the attenuation value, which is dependent on the attenuation coefficient present between the two acoustic transducers, by way of a suitable calculation of the two determined amplitude values. The signal processing unit is designed to determine the attenuation value according to any one or more of a number of different possible calculation rules. A few of these calculation rules are described hereinafter.

In one version, the signal processing unit is designed to determine the attenuation value D as a function of the first amplitude value and the second amplitude value, according to the following formula:

$$D = \frac{A(f_1)}{A(f_2)}, \quad (2)$$

where $A(f_1)$ is the first amplitude value of the first signal portion of the received acoustic signal, $A(f_2)$ is the second amplitude value of the second signal portion of the received acoustic signal, $f_1$ is the first frequency, and $f_2$ is the second frequency. In this version, the attenuation value D is dependent on a change of the attenuation coefficient. The first signal portion and the second signal portion preferably have the same amplitude at the time they are emitted. Otherwise, the formula (2) preferably includes a correction factor by which the differences between the transmission amplitudes of the two signal portions can be corrected.

This version has the advantage that the signal processing unit can have a comparatively simple design because the calculation simply involves the calculation of quotients.

In another version of the implant, the signal processing unit is designed to determine the attenuation value D as a function of the first amplitude value and the second amplitude value according to the following formula:

$$D = A(f_1) - A(f_2), \quad (3)$$

where $A(f_1)$ is the first amplitude value of the first signal portion of the received acoustic signal, $A(f_2)$ is the second amplitude value of the second signal portion of the received acoustic signal, $f_1$ is the first frequency, and $f_2$ is the second frequency. For example, $A(f_1)$ and $A(f_2)$ are logarithmized amplitude values. This version also has the advantage that the signal processing unit can have a comparatively simple design because the calculation simply involves the calculation of the difference. In an alternative version, the signal processing unit determines the attenuation value according to $$D = \frac{A(f_1) - A(f_2)}{A(f_1)}, \quad (4)$$

this being a difference that is standardized to the first amplitude value.

In a further version of the implant, the signal processing unit is designed to determine the attenuation value D as a function of the first amplitude value and the second amplitude value according to the following formula:

$$D = \frac{A(f_1) - A(f_2)}{f_2 - f_1}, \quad (5)$$

where $A(f_1)$ is the first amplitude value of the first signal portion of the received acoustic signal, $A(f_2)$ is the second amplitude value of the second signal portion of the received acoustic signal, $f_1$ is the first frequency, and $f_2$ is the second frequency.

In a preferred version of the implant, the signal processing unit is designed to determine a first reduction value as a function of a first reduction of a first signal portion having a first frequency and a second reduction value reducing a second amplitude of a second signal portion having a second frequency for a received signal, and to determine the attenuation value D as a function of the determined first and second reduction values according to the following formula:

$$D = -\frac{a(f_2) - a(f_1)}{r(f_2 - f_1)}, \quad (6)$$

where $a(f_1)$ is the first reduction value of the first signal portion of the received acoustic signal, $a(f_2)$ is the second reduction value of the second signal portion of the received acoustic signal, $f_1$ is the first frequency, $f_2$ is the second frequency, and r is a signal path of the emitted acoustic signal. The signal path is identical to the distance between the two acoustic transducers when the second acoustic transducer is the receiving acoustic transducer, and it is identical to double the distance between the two acoustic transducers when the second acoustic transducer is a reflector.

In this version, the attenuation value D is identical for the attenuation coefficient between the first and second acoustic transducers. The calculation rule (6) is obtained by adding two formulas (1), of which the first relates to the first frequency and the second relates to the second frequency, where k=1. An advantage of this version is the high accuracy of the attenuation value.

The signal processing unit in the version described above is preferably designed to determine the distance r as a function of a signal travel time of the emitted acoustic signal.

In a particularly preferred version, the implant comprises a cardioverter/defibrillator. The cardioverter/defibrillator is preferably designed to conduct cardiac rhythm therapy as a function of the prediction signal.

In a further version, the implant is configured to carry out cardiac resynchronization therapy (CRT), and/or to monitor one or more physiological parameters.

Further versions of the invention relate to an implantable cardiac pacemaker, a CRT implant, an implantable cardioverter/defibrillator, a monitoring implant, or another implantable medical device, which includes at least two of the acoustic transducers described above and a signal processing unit described above, which are designed to act and interact in the manner described above.

In all versions, the signal processing unit is preferably designed to determine the attenuation value multiple consecutive times and average the values, and to compare the average attenuation value to the threshold value. In this way, potential variations of the distance between the two acoustic transducers, such as those caused by a respiratory cycle, are compensated for and thereby the specificity of the prediction signal is further increased.

The implant may also include a memory for storing measured values, such as the attenuation value, the reduction values, and/or the amplitude values.

The signal processing unit is further preferably designed to periodically determine the attenuation value, e.g., at times having the same intervals between each other. As an alternative, the signal processing unit can determine the attenuation value at predetermined fixed times.

The signal processing unit can therefore determine the attenuation value periodically at least once during a certain time period; periodically within a certain time period continuously for a defined duration; at established times such as day, night or a time of day; optionally one time or continuously for a defined time duration; under certain conditions such as lying or standing, or prompted by certain events such as a change in the activity of the patient or a change in the position of the patient.

The implant can emit an acoustic signal at a certain time during the cardiac cycle, such as a diastole, so as to eliminate the potential interfering influence of the cardiac contraction.

The signal processing unit is further preferably designed to use the determined attenuation value not only to derive the prediction signal, but to derive further diagnostic parameters, for example statistical parameters, breathing amplitudes, parameters quantifying (for example) the ratio of lying to standing, and further trends and trend parameters.

In all versions of the implant, the threshold value can optionally be fixed or adaptive. An adaptive threshold value, for example, is a patient-individual threshold value which the signal processing unit sets as a function of a condition of the patient.

The invention also encompasses systems which incorporate the implant, such as an implant as described above, a patient device communicating with the implant, and a processor station in communication with the patient device. The implant of the present invention can thus also be incorporated in a home monitoring system. For example, the implant can include an additional transceiver which is designed to transmit the determined attenuation value (and/or the reduction values, and/or the amplitude values, and/or the prediction signal) to the patient device associated with the patient. The patient device, in turn, can transmit the determined attenuation value (and/or the reduction values, and/or the amplitude values, and/or the prediction signal) to the processor station communicating with the patient device. In this way, the implant also benefits from the many advantages that a home monitoring system offers. For example, the patient device and/or the processor station may assume part of the signal processing operation, transmit a certain threshold value to the implant, or store and compare evaluation data of a plurality of implants.

Further advantages of the invention will be described below in connection with the drawing.

BRIEF DESCRIPTION OF THE DRAWING

FIG. 1 shows a version 500 of a system incorporating an implant as described above.

DETAILED DESCRIPTION OF PREFERRED VERSIONS OF THE INVENTION

Referring to FIG. 1, the system 500 comprises a version 200 of the implant, a patient device 300, and a processor station 400. The implant 200 is used to predict decompensation of the heart 100 and is disposed in the thorax of the patient. The implant 200 comprises a first acoustic transducer 210 and a second acoustic transducer 220, which are matched to each other. The first acoustic transducer 210 is disposed in the housing of the implant. The second acoustic transducer 220 is disposed outside of the housing of the implant 200.

In the version illustrated in FIG. 1, the first acoustic transducer 210 is designed as a transmitting and receiving transducer and the second acoustic transducer 220 is designed as a reflector. The second acoustic transducer 220 is disposed in the vicinity of the heart 100, for example on an ICD electrode located there. In order to determine an attenuation value that is dependent on the acoustic attenuation coefficient present between the two acoustic transducers 210, 220, the first acoustic transducer 210 emits an acoustic signal 230. As an example, the first acoustic transducer initially emits a first signal portion having a first frequency of (for example) approximately 30 kHz, and thereafter a second signal portion having a second frequency of (for example) approximately 250 kHz. As an alternative, the first acoustic transducer 210 can emit a short broadband pulse. The first acoustic transducer 210 can be provided by a piezo crystal, a piezoelectric polymer, a micromechanical transducer, or other suitable devices.

The emitted acoustic signal 230 then passes at least part of the pulmonary tissue of the patient, which is not shown in FIG. 1. The second acoustic transducer 220, which is disposed in the vicinity of the heart 100 and takes the form of a reflector, reflects the acoustic signal 230 back to the first acoustic transducer 210.

The first acoustic transducer 210 is operatively connected to a signal processing unit 240. Filter amplifiers, which are not shown in FIG. 1, may be provided in the implant for prior signal processing. The signal processing unit 240 is designed to determine an attenuation value as a function of the attenuation of a received acoustic signal 250 compared to the originally emitted acoustic signal 230, and to emit a prediction signal as a function of a comparison of the attenuation value to a threshold value. The prediction signal is suited to indicate the development of decompensation.

For example, the signal processing unit 240 can be designed to determine the attenuation value according to one of the formulas (2) to (6) provided above. The implant 200 is designed to transmit the determined attenuation value and/or the prediction signal to the patient device 300. The patient device 300 communicates with the processor station 400 so as to evaluate and further process the data generated by the implant 200.

Preferred versions of the invention have been described above for purposes of illustration, and numerous modifications and variations to these versions are possible. The invention is not intended to be limited to the preferred versions, but rather is intended to be limited only by the claims set out below. Thus, the invention encompasses all different versions that fall literally or equivalently within the scope of these claims.

The invention claimed is:

1. An implant for predicting decompensation of the heart of a patient, the implant including:
   a. a first acoustic transducer configured to emit an acoustic signal having a first signal portion having a first frequency;
   b. a second acoustic transducer configured to:
      (1) receive and re-emit, or
      (2) receive and reflect,
      the acoustic signal emitted by the first acoustic transducer, such that the first acoustic transducer can receive the acoustic signal; and
   c. a signal processing unit:

(1) in communication with at least one of the acoustic transducers, and
(2) configured to:
    (a) determine an attenuation value representing the attenuation of the acoustic signal, the attenuation value being determined as a function of a duration of the acoustic signal received at the first acoustic transducer as compared to a duration of the acoustic signal emitted by the first acoustic transducer and
    (b) generate a prediction signal from the attenuation value, the prediction signal being indicative of decompensation of the heart.

2. The implant of claim 1 wherein the first acoustic transducer, second acoustic transducer, and signal processing unit are included as components of a cardioverter/defibrillator.

3. The implant of claim 2 wherein the cardioverter/defibrillator further includes:
  a. a housing wherein the first acoustic transducer is located, and
  b. a lead extending from the housing, wherein the second acoustic transducer is situated on or within the lead.

4. The implant of claim 3 wherein the lead further includes an electrode thereon, the electrode being configured to deliver electrical stimulation to any surrounding tissue.

5. The implant of claim 1 further including:
  a. a patient device spaced from, and configured to communicate with, the implant, and
  b. a processor station distant from, and configured to communicate with, the patient device.

6. The implant of claim 1 wherein the prediction signal is generated as a function of a comparison of the attenuation value to a threshold value.

7. The implant of claim 1 wherein the first acoustic transducer is configured to emit an acoustic signal having:
  a. a first signal portion having a first frequency, and
  b. a second signal portion having a second frequency which is different from the first frequency.

8. The implant of claim 7 wherein the signal processing unit is further configured to determine the attenuation value as a function of:
  a. the attenuation of the first signal portion received at the first acoustic transducer as compared to the first signal portion emitted by the first acoustic transducer, and
  b. the attenuation of the second signal portion received at the first acoustic transducer as compared to the second signal portion emitted by the first acoustic transducer.

9. The implant of claim 7 wherein the signal processing unit is further configured to determine:
  a. a first amplitude value as a function of a first amplitude of the first signal portion received at the first acoustic transducer,
  b. a second amplitude value as a function of a second amplitude of the second signal portion received at the first acoustic transducer,
  c. the attenuation value as a function of the first and second amplitude values.

10. The implant of claim 9 wherein the signal processing unit is further configured to determine the attenuation value D as a function of the first amplitude value and the second amplitude value in accordance with:

$$D = \frac{A(f_1)}{A(f_2)},$$

where $A(f_1)$ is the first amplitude value, $A(f_2)$ is the second amplitude value, $f_1$ is the first frequency, and $f_2$ is the second frequency.

11. The implant of claim 9 wherein the signal processing unit is further configured to determine the attenuation value D as a function of the first amplitude value and the second amplitude value in accordance with:

$$D = A(f_1) - A(f_2),$$

where $A(f_1)$ is the first amplitude value, $A(f_2)$ is the second amplitude value, $f_1$ is the first frequency, and $f_2$ is the second frequency.

12. The implant of claim 9 wherein the signal processing unit is further configured to determine the attenuation value D as a function of the first amplitude value and the second amplitude value in accordance with:

$$D = \frac{A(f_1) - A(f_2)}{A(f_1)},$$

where $A(f_1)$ is the first amplitude value, $A(f_2)$ is the second amplitude value, $f_1$ is the first frequency, and $f_2$ is the second frequency.

13. The implant of claim 9 wherein the signal processing unit is further configured to determine the attenuation value D as a function of the first amplitude value and the second amplitude value in accordance with:

$$D = \frac{A(f_1) - A(f_2)}{f_2 - f_1},$$

where $A(f_1)$ is the first amplitude value, $A(f_2)$ is the second amplitude value, $f_1$ is the first frequency, and $f_2$ is the second frequency.

14. The implant of claim 7 wherein the signal processing unit is further configured to determine:
  a. a first reduction value representing a reduction in the amplitude of the first signal portion received at the first acoustic transducer as compared to the amplitude of the first signal portion emitted by the first acoustic transducer, and
  b. a second reduction value representing a reduction in the amplitude of the second signal portion received at the first acoustic transducer as compared to the amplitude of the second signal portion emitted by the first acoustic transducer,
  c. the attenuation value D as a function of the determined first and second reduction values in accordance with:

$$D = -\frac{a(f_2) - a(f_1)}{r(f_2 - f_1)},$$

where $a(f_1)$ is the first reduction value, $a(f_2)$ is the second reduction value, $f_1$ is the first frequency, $f_2$ is the second frequency, and r is the signal path of an emitted acoustic signal.

15. The implant of claim 7 wherein the first acoustic transducer is configured to emit the first signal portion and the second signal portion at least partially simultaneously.

16. The implant of claim 7 wherein the first acoustic transducer is configured to emit the first signal portion and the second signal portion in close succession.

17. The implant of claim 7 further including a filter between the first acoustic transducer and the signal processing unit, the filter being configured to divide a received acoustic signal into:
   a. a first received signal portion having the first frequency, and
   b. a second received signal portion having the second frequency.

18. The implant of claim 1, further including a position sensor configured to generate a position signal dependent on the position of the patient, wherein the signal processing unit is further configured to generate the prediction signal as a function of the attenuation value and the position signal.

19. An implant for predicting decompensation of the heart of a patient, the implant including:
   a. an emitting acoustic transducer configured to emit an acoustic signal;
   b. a receiving acoustic transducer configured to receive the emitted acoustic signal and return the emitted acoustic signal to the emitting acoustic transducer; and
   c. a signal processing unit:
      (1) in communication with at least one of the acoustic transducers, and
      (2) configured to generate an indication of decompensation of the heart as a function of an attenuation value for the acoustic signal determined as a function of a duration of the returned acoustic signal as compared to a duration of the emitted acoustic signal.

* * * * *